(12) United States Patent
Krutak et al.

(10) Patent No.: US 10,030,036 B2
(45) Date of Patent: Jul. 24, 2018

(54) METHOD AND DYES FOR DETECTING AND DESTROYING CANCER CELLS

(75) Inventors: James J. Krutak, Colorado Springs, CO (US); Lyle Small, Colorado Springs, CO (US); Maged Henary, Lawrenceville, GA (US); Gabor Patonay, Conyers, GA (US)

(73) Assignee: Lahjavida, LLC, Colorado Springs, CO (US)

( * ) Notice: Subject to any disclaimer, the term of this patent is extended or adjusted under 35 U.S.C. 154(b) by 601 days.

(21) Appl. No.: 12/778,569

(22) Filed: May 12, 2010

(65) Prior Publication Data
US 2015/0376209 A1 Dec. 31, 2015

Related U.S. Application Data

(60) Provisional application No. 61/178,835, filed on May 15, 2009.

(51) Int. Cl.
| | |
|---|---|
| *A61N 1/40* | (2006.01) |
| *C07F 1/00* | (2006.01) |
| *A61K 49/00* | (2006.01) |
| *A61K 41/00* | (2006.01) |
| *C09B 23/01* | (2006.01) |
| *C09B 23/08* | (2006.01) |

(52) U.S. Cl.
CPC ............ *C07F 1/00* (2013.01); *A61K 41/0052* (2013.01); *A61K 41/0057* (2013.01); *A61K 49/0032* (2013.01); *A61K 49/0093* (2013.01); *A61N 1/406* (2013.01); *C09B 23/0016* (2013.01); *C09B 23/0025* (2013.01); *C09B 23/0066* (2013.01); *C09B 23/086* (2013.01)

(58) Field of Classification Search
None
See application file for complete search history.

(56) References Cited

U.S. PATENT DOCUMENTS

| | | | | |
|---|---|---|---|---|
| 2008/0160090 A1* | 7/2008 | Oraevsky | ............ | A61K 41/0052 424/489 |
| 2012/0251453 A1* | 10/2012 | Fukuda | ............ | A61K 47/48276 424/9.1 |
| 2013/0039858 A1* | 2/2013 | Brown | ............. | G01N 33/54346 424/9.3 |

FOREIGN PATENT DOCUMENTS

WO   WO2009012109   * 1/2009   ........... C07D 403/02

OTHER PUBLICATIONS

Yang et al (Near IR heptamethine cyanine dye-mediated cancer imaging. Clin Cancer Res. May 15, 2010;16(10):2833-44. doi:10.1158/1078-0432.CCR-10-0059. Epub Apr. 21, 2010).*
Provisional Application 61309282 (2010).*
Pham et al (Synthesis and Application of a Water-Soluble Near-Infrared Dye for Cancer Detection Using Optical Imaging. Bioconjugate Chem., 2005, 16 (3), pp. 735-740).*
Fu et al (Plasmonic Enhancement of Single-Molecule Fluorescence Near a Silver Nanoparticle. J Fluoresc. Nov. 2007 ; 17(6): 811-816).*

* cited by examiner

*Primary Examiner* — Jake M Vu
(74) *Attorney, Agent, or Firm* — Craig R. Miles; CR Miles P.C.

(57) ABSTRACT

This invention relates to new carbocyanine dye compositions, pharmaceutical compositions comprising such compositions, methods of detecting via near infrared fluorescent imaging incipient cancer cells and selective destruction of cancer cells identified by administration of such pharmaceutical compositions. A method of detecting and destroying cancer cells includes introducing a gold dye into an organism suspected of having a cancer cell. The gold dye is a carbocyanine dye covalently attached to a gold nanoparticle. A near infrared light is shined on a region suspected of having the cancer cell. Fluorescence from the gold dye is detected. A beam of radio frequency energy is directed at the region to induce hyperthermia in the cancer cell. The carbocyanine dye has the most basic structure of MHI-148 and structures 6 and 22 with a $Au_n$—[$CH_2(CH_2)_9CH_2$—($OCH_2CH_2$)$_4$O]$COCH_2CH_2$-phenyl-O group on a cyclohexene ring that imparts activity to the cancer cell binding and destruction processes.

22 Claims, 1 Drawing Sheet

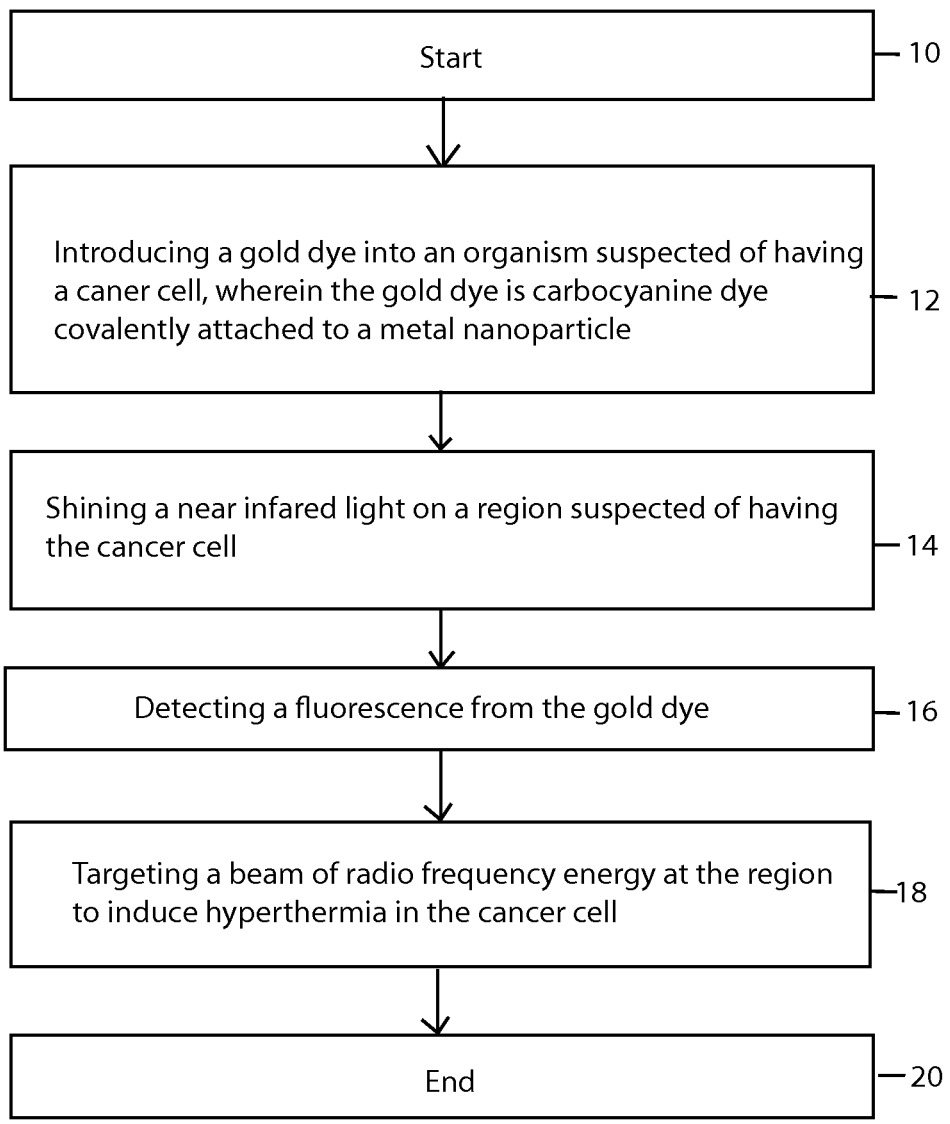

METHOD AND DYES FOR DETECTING AND DESTROYING CANCER CELLS

RELATED APPLICATIONS

The present invention claims priority on provisional patent application, Ser. No. 61/178,835, filed on May 15, 2009, entitled "Novel Carbocyanine Dyes Bonded to Gold Nano-Particles for the Detection and Therapeutic Treatment of Cancer" and is hereby incorporated by reference.

STATEMENT REGARDING FEDERALLY SPONSORED RESEARCH

Not Applicable

THE NAMES OF THE PARTIES TO A JOINT RESEARCH AGREEMENT

The present invention was co-developed by CTI and KPS Technologies, LLC.

REFERENCE TO A SEQUENCE LISTING, A TABLE, OR A COMPUTER PROGRAM LISTING

Not Applicable

BACKGROUND OF THE INVENTION

Traditionally cancer has been treated with general radiation treatment and chemotherapy. Both of which have been shown to have a number of side effects. For instance, radiation treatment can result in loss of hair, nausea, and low white cell counts and other side effects such as abdominal pain, nausea, and vomiting. As a result, there has been a constant desire to find cancer treatments with fewer side effects. One solution has been to create RF (Radio Frequency) absorption enhancers that are attached to antibodies that attach to cancer cells. These RF absorption enhancers are very small tuned circuits that induce hyperthermia in the cancer cells to which they are attached when RF energy is directed at them. Unfortunately, these RF absorption enhancers do not provide feedback on where the cancer cells are located. As a result, the RF energy cannot be highly directed to the area with the cancer cells. In addition, these RF absorption enhancers are complex to manufacture.

Thus, there exists a need for an improved method of treating cancer that does not have the side effects of chemotherapy or high intensity radiation treatment and in which the energy used to kill the cancer cells can be highly targeted.

BRIEF SUMMARY OF INVENTION

This invention relates to new carbocyanine dye compositions, pharmaceutical compositions comprising such compositions, methods of detecting via near infrared fluorescent imaging incipient cancer cells and selective destruction of cancer cells identified by administration of such pharmaceutical compositions.

A method of detecting and destroying cancer cells includes introducing a gold dye into an organism suspected of having a cancer cell. The gold dye is a carbocyanine dye covalently attached to a gold nanoparticle. A near infrared excitation light source is scanned on a region suspected of having the cancer cells. Fluorescence emitted from the excited gold dye is detected by near infrared imaging techniques. A beam of radio frequency energy is directed at the near infrared fluorescence imaged region to induce hyperthermia in the cancer cell. In one embodiment, the carbocyanine dye has the most basic structure of MHI-148 with a $Au_n$—[S—$CH_2(CH_2)_9CH_2$—$(OCH_2CH_2)_4O$] $COCH_2CH_2$-phenyl-O group on a cyclohexene ring that imparts activity to the cancer cell binding and destruction processes. Note that multiple gold atoms may be attached to the phenyl-O group. In another embodiment, silver, copper or another metal may be substituted for gold.

These gold dyes are easy to produce and comparatively inexpensive. The gold dye is rapidly eliminated from the healthy cells and tissue either via urinary and fecal routes with no accumulation in the healthy tissue. Certain gold dye structures with optimized total charge on the molecule have been discovered that avoid passage through the liver during clean out from the body. Any side effects of the process are therefore minimized.

BRIEF DESCRIPTION OF THE SEVERAL VIEWS OF THE DRAWINGS

FIG. 1 is a flow chart of the steps used in a method for detecting and destroying cancer cells.

DETAILED DESCRIPTION OF THE INVENTION

The invention relates to new carbocyanine dye compositions, pharmaceutical compositions comprising such compositions, methods of detecting via near infrared fluorescent imaging incipient cancer cells and selective destruction of cancer cells identified by administration of such pharmaceutical compositions.

FIG. 1 is a flow chart of the steps used in a method for detecting and destroying cancer cells. The process starts, step 10, by introducing a gold dye into an organism suspected of having cancer at step 12. The gold dye is a carbocyanine dye covalently attached to a metal nanoparticle. In a preferred embodiment, the metal nanoparticle is gold. Near infrared light is shone on a region of the organism suspected of having cancer cells at step 14. Fluorescence from the gold dye is detected at step 16. The gold dye adheres to cancer cells and any excess of the gold dye is quickly flushed from organism's body. As a result, fluorescence only occurs in areas that have cancer cells. At step 18, a beam of radio frequency energy is directed at the region to induce hyperthermia in the cancer cell, which ends the process at step 20.

The gold dye is flushed from the body along with the dead cancer cells. A number of mechanisms have been hypothesized as to why the gold dye induces hyperthermia and this invention is not limited to any specific theory. It is known that metal particles less than 100 micrometers are heated by microwave energy. One theory is that the metal nanoparticles are directly heated by the microwave energy. It is possible that the magnetic field of the radio frequency energy induces inductive heating of the metal nanoparticles. The optimum frequency of the radio waves can be determined by measuring the heat output versus the frequency. The heat output can be measured using an infrared thermal camera.

The carbocyanine dye of the gold dye is known to absorb light in the near infrared spectrum from 680 to 1200 nm and to fluoresce in the near infrared spectrum at longer wavelengths. These carbocyanine dyes have been shown to selectively bind to cancer cells and cancerous tissue.

Specific structures were designed that selectively bind to cancer cells and cancerous tissue in-vitro and in-vivo after covalent attachment of one or more carbocyanine dye molecule to gold nanoparticles. Gold particles that do not have dyes attached to their surface are separated and not used. A specific dye composition that facilitates the transport of gold particles synthesized according to Scheme 1 selectively binds to cancer cells in-vivo and accumulate in tumors. Any non-binding gold dye cleans out rapidly without toxic effects. The example dye shown here contains bromide counter anions but in manufactured pharmaceutical compositions the bromide will be changed to a pharmaceutically acceptable carrier or excipient such as citrate, tartrate, etc. Such carriers or excipients refer to an excipient that can be included in the compositions of the invention and that causes no significant adverse toxicological effects to the patient.

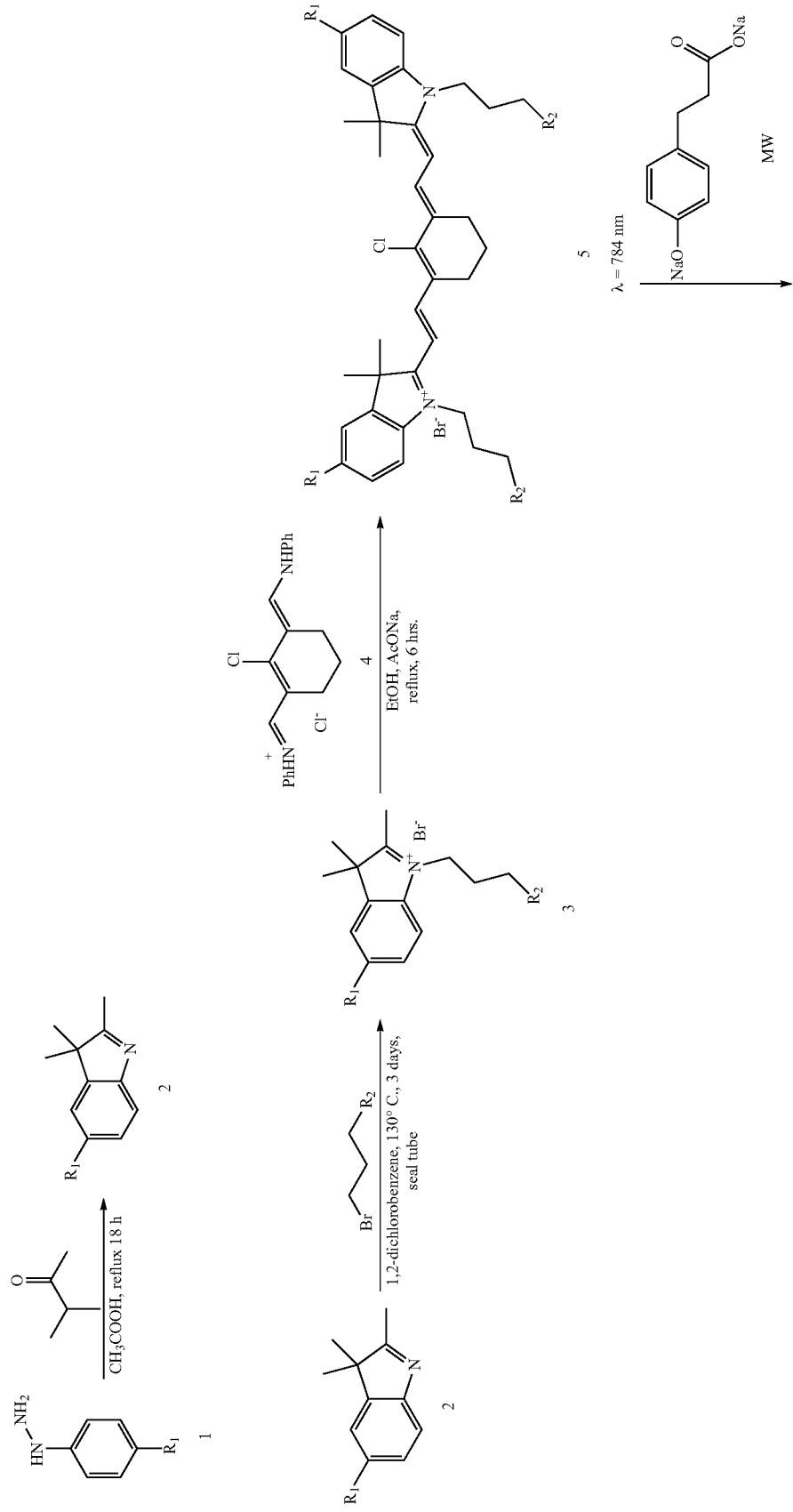

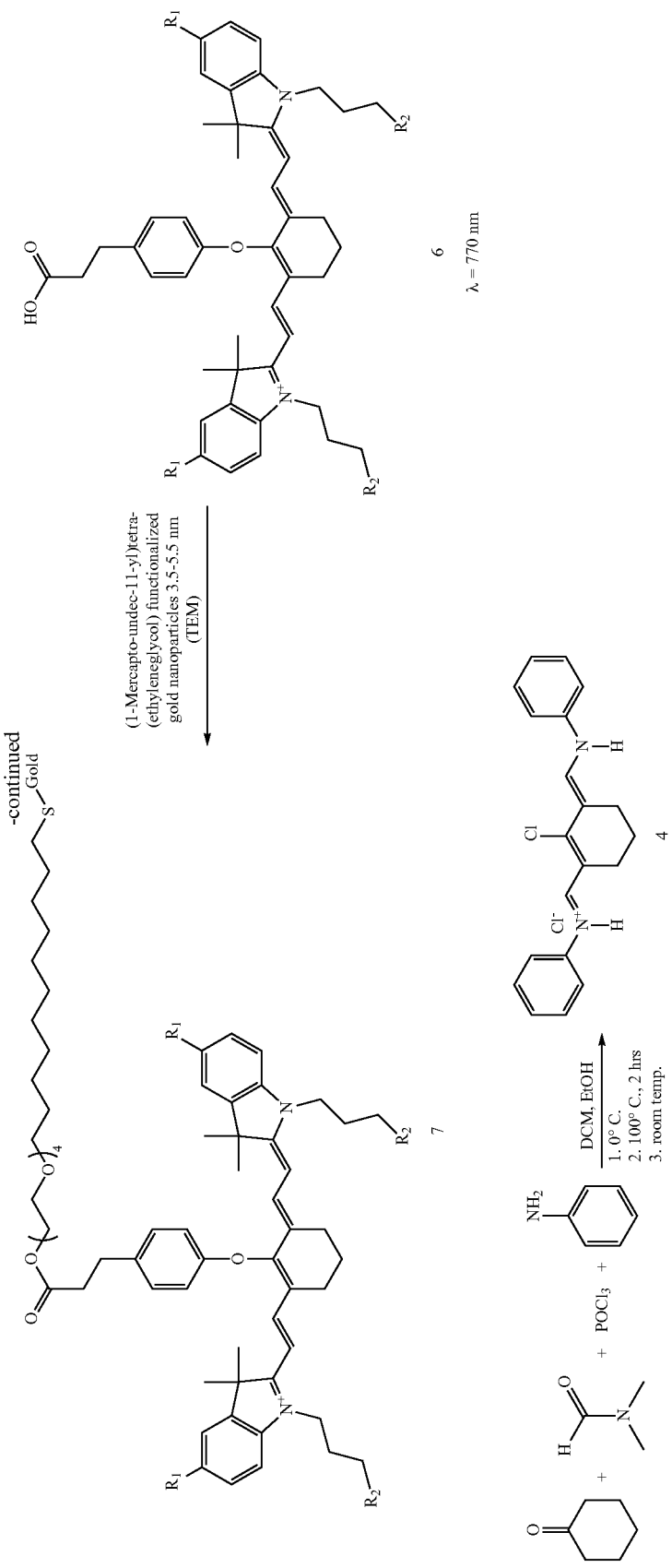

Scheme 2
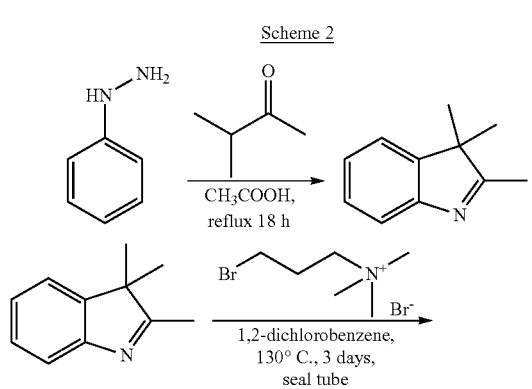
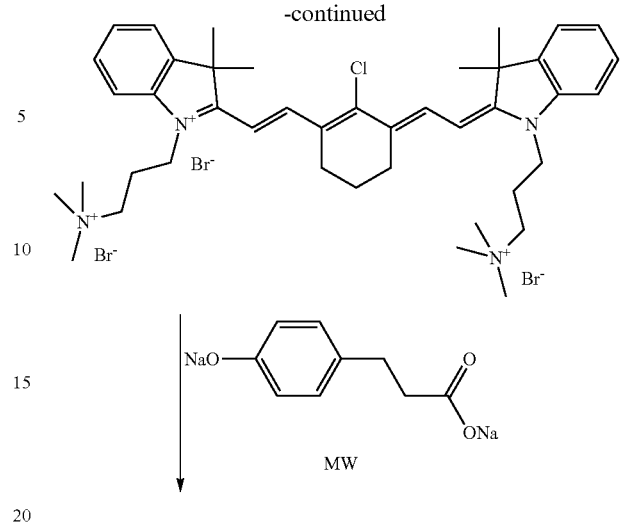
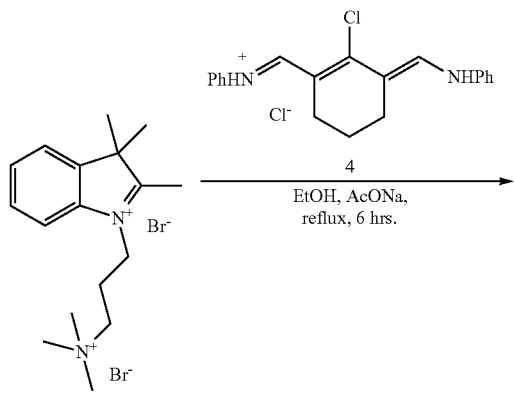
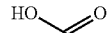
Structure 6
Scheme 3
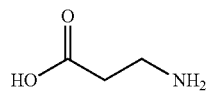
17
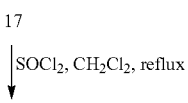

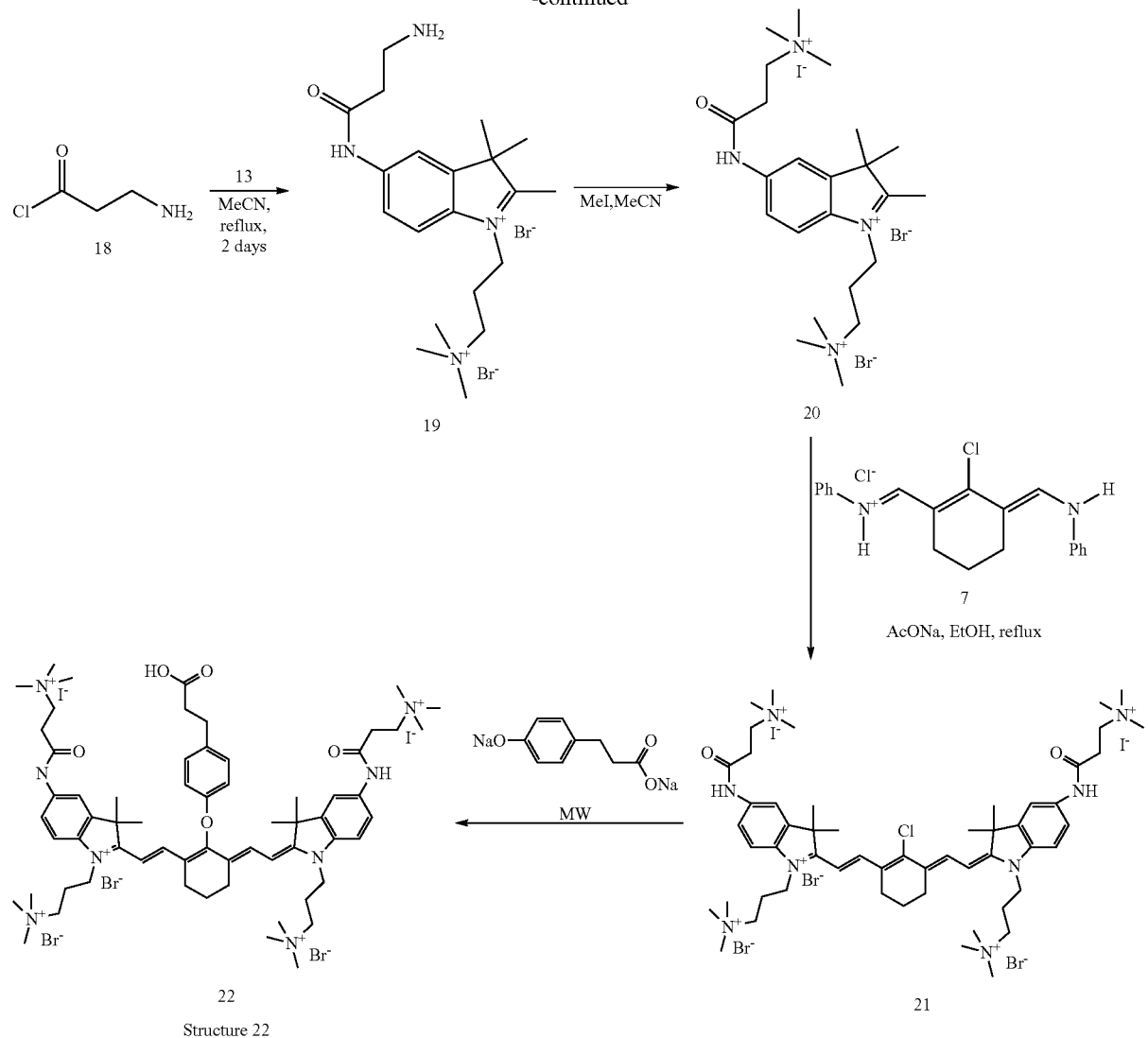
Structure 22

Scheme 4
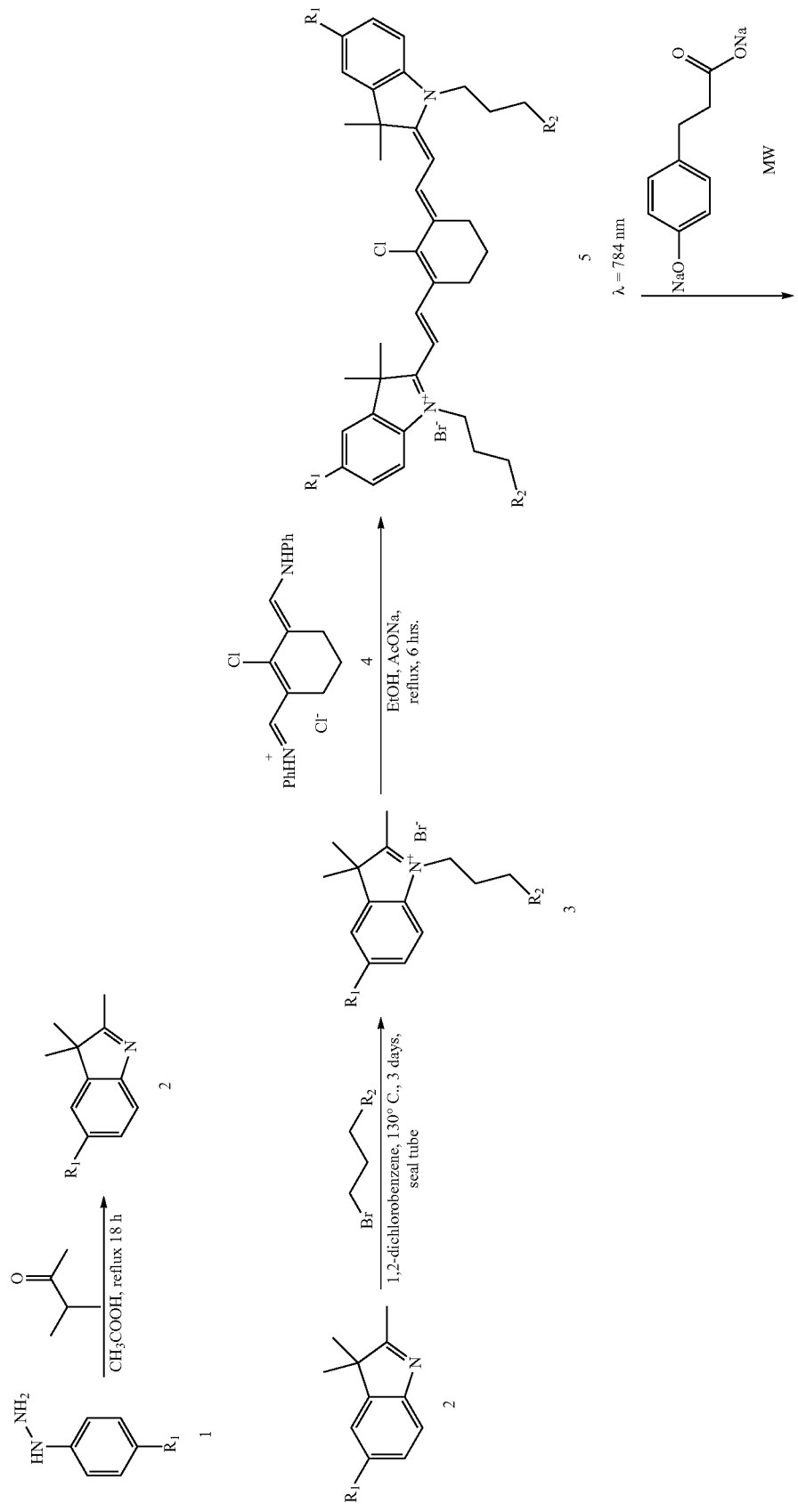

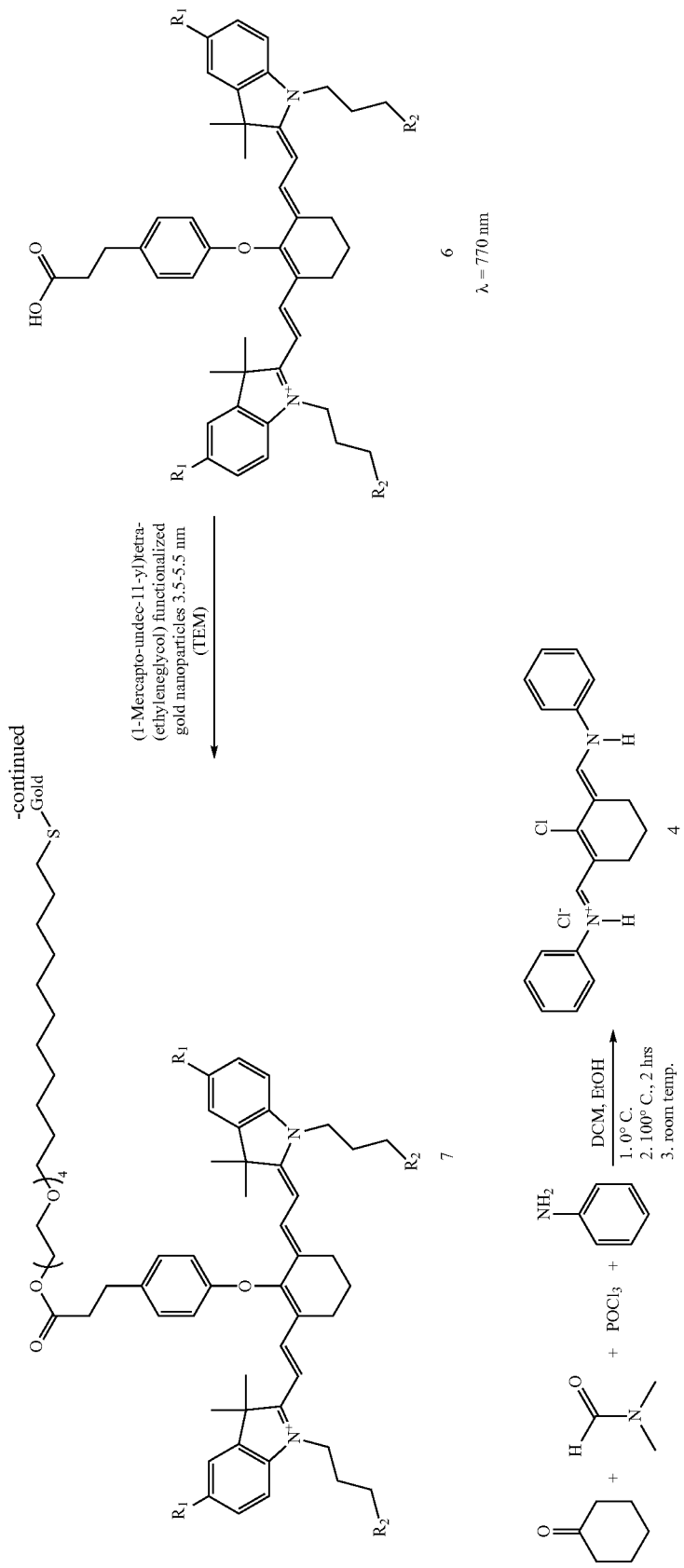
R1: H, CN, COOH, Cl, OH, OMe
R2: H, SO3-, OH, N+R3, COOH

Note that the final structure of scheme 2 is structure 6 and the final structure of scheme 3 is structure 22.

The preferred formula 1-8 of the carbocyanine dyes for the present invention have a $Au_n$—[S—$CH_2(CH_2)_9CH_2$—($OCH_2CH_2)_4O$]$COCH_2CH_2$-phenyl-O group on the cyclohexene or cyclopentene ring of the heptacyanine structures disclosed that may have a significant role in the described retaining and toxicity properties. In the preferred embodiment, heptamethine cyanine dyes are synthesized. The preferred heptamethine cyanines absorb light efficiently and have maximum absorption wavelengths in the region of 780 to 1100 nm. This wavelength is suitable for reducing background fluorescence in vivo and corresponds to the radiation wavelength of the GaAlAs diode laser and other semiconductor light sources.

Some of these compounds in formula 1-8 and the compounds shown in Scheme 1 have variable water solubility, near infrared fluorescent spectral properties suitable for in-vivo tissue imaging (e.g. MHI-148 has $\lambda_{max}$ absorption 780 nm and high intensity $\lambda_{max}$ emission 800 nm (FIG. 1)), and have been tested to have similar activities in near infrared fluorescent imaging of tumor cells and inhibiting tumor cell growth in vitro, and permit selective destruction of any gold labeled cancer cells via radiofrequency treatment. The solubility of the labeled gold particles may be controlled by the dye molecules attached to the surface of gold particles or by additional solubilization groups attached to the gold particle surface as it is described by the literature or by prior art. Biodistribution of these gold particles are determined by the molecules attached to the gold particle surface and particle size.

Formula 1

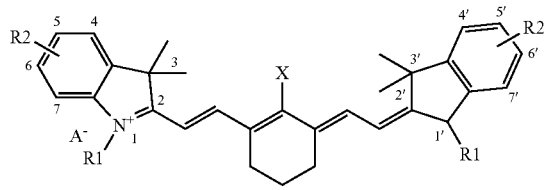

R2=H, EWG, EDG in 4, 4', 5, 5', 6, 6', 7, 7', 8, 8', 9, 9' positions
R1=H, Alkyl, Aryl, Aralkyl, $RSO_3^-$, $RCOO^-$, $RNH_2$
A=I, Cl, Br, $OSO_2Aryl$, $OSO_2R$, $BF_4$, $ClO_4$, or pharmaceutically acceptable carrier anion such as citrate, tartrate
X=$Au_n$—[S—$CH_2(CH_2)_9CH_2$—$(OCH_2CH_2)_4O$]$COCH_2CH_2$-phenyl-O, or
$Au_n$—[S—$(CH_2)_9$—S n=a subscript meaning n=1-20 atoms Formula 2

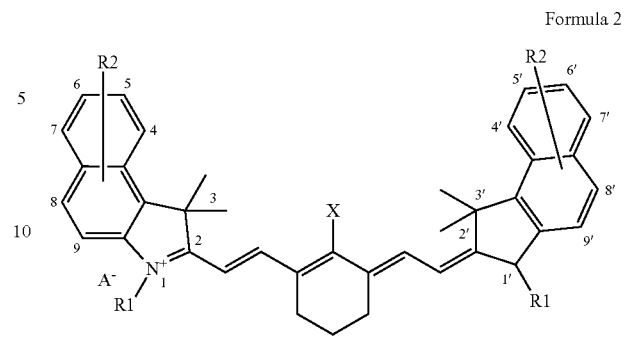

R2=H, EWG, EDG in 4, 4', 5, 5', 6, 6', 7, 7', 8, 8', 9, 9' positions
R1=H, Alkyl, Aryl, Aralkyl, $RSO_3^-$, $RCOO^-$, $RNH_2$
A=I, Cl, Br, $OSO_2Aryl$, $OSO_2R$, $BF_4$, $ClO_4$, or pharmaceutically acceptable carrier anion such as citrate, tartrate
X=$Au_n$—[S—$CH_2(CH_2)_9CH_2$—$(OCH_2CH_2)_4O$]$COCH_2CH_2$-phenyl-O, or
$Au_n$—[S—$(CH_2)_9$—S n=a subscript meaning n=1-20 atoms Formula 3

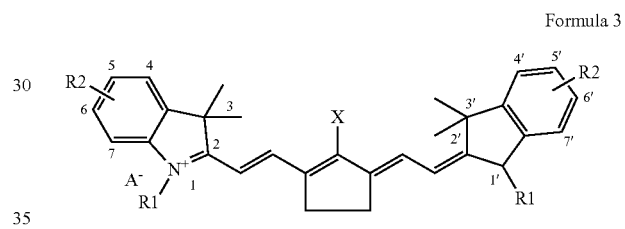

R2=H, EWG, EDG in 4, 4', 5, 5', 6, 6', 7, 7', 8, 8', 9, 9' positions
R1=H, Alkyl, Aryl, Aralkyl, $RSO_3^-$, $RCOO^-$, $RNH_2$
A=I, Cl, Br, $OSO_2Aryl$, $OSO_2R$, $BF_4$, $ClO_4$, or pharmaceutically acceptable carrier anion such as citrate, tartrate
X=$Au_n$—[S—$CH_2(CH_2)_9CH_2$—$(OCH_2CH_2)_4O$]$COCH_2CH_2$-phenyl-O, or
$Au_n$—[S—$(CH_2)_9$—S n=a subscript meaning n=1-20 atoms Formula 4

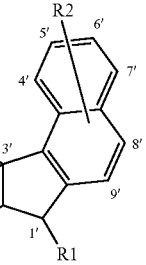

R2=H, EWG, EDG in 4, 4', 5, 5', 6, 6', 7, 7', 8, 8', 9, 9' positions
R1=H, Alkyl, Aryl, Aralkyl, $RSO_3^-$, $RCOO^-$, $RNH_2$
A=I, Cl, Br, $OSO_2Aryl$, $OSO_2R$, $BF_4$, $ClO_4$, or pharmaceutically acceptable carrier anion such as citrate, tartrate X=Au$_n$—[S—CH$_2$(CH$_2$)$_9$CH$_2$—(OCH$_2$CH$_2$)$_4$O]
COCH$_2$CH$_2$-phenyl-O, or
Au$_n$—[S—(CH$_2$)$_9$—S n=a subscript meaning n=1-20 atoms

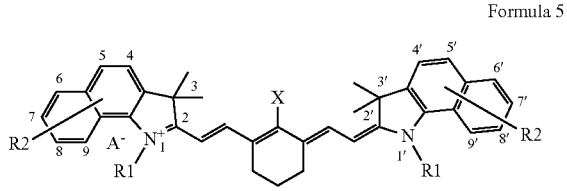

Formula 5

R2=H, EWG, EDG in 4, 4', 5, 5', 6, 6', 7, 7', 8, 8', 9, 9° positions
R1=H, Alkyl, Aryl, Aralkyl, RSO$_3^-$, RCOO$^-$, RNH$_2$
A=I, Cl, Br, OSO$_2$Aryl, OSO$_2$R, BF$_4$, ClO$_4$, or pharmaceutically acceptable carrier anion such as citrate, tartrate
X=Au$_n$—[S—CH$_2$(CH$_2$)$_9$CH$_2$—(OCH$_2$CH$_2$)$_4$O]
COCH$_2$CH$_2$-phenyl-O, or
Au$_n$—[S—(CH$_2$)$_9$—S n=a subscript meaning n=1-20 atoms

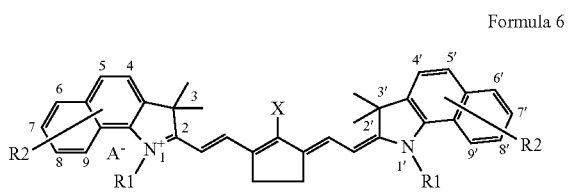

Formula 6

R2=H, EWG, EDG in 4, 4', 5, 5', 6, 6', 7, 7', 8, 8', 9, 9' positions
R1=H, Alkyl, Aryl, Aralkyl, RSO$_3^-$, RCOO$^-$, RNH$_2$
A=I, Cl, Br, OSO$_2$Aryl, OSO$_2$R, BF$_4$, ClO$_4$, or pharmaceutically acceptable carrier anion such as citrate, tartrate
X=Au$_n$—[S—CH$_2$(CH$_2$)$_9$CH$_2$—(OCH$_2$CH$_2$)$_4$O]
COCH$_2$CH$_2$-phenyl-O, or
Au$_n$—[S—(CH$_2$)$_9$—S n=a subscript meaning n=1-20 atoms

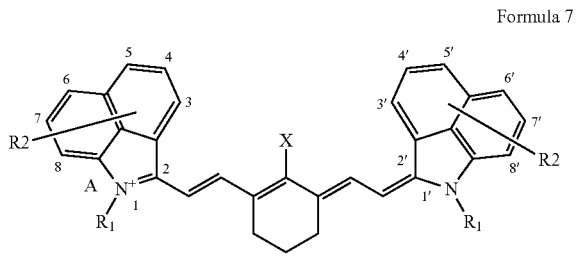

Formula 7

R2=H, EWG, EDG in 3, 3', 4, 4', 5, 5', 6, 6', 7, 7', 8, 8' positions
R1=H, Alkyl, Aryl, Aralkyl, RSO$_3^-$, RCOO$^-$, RNH$_2$
A=I, Cl, Br, OSO$_2$Aryl, OSO$_2$R, BF$_4$, ClO$_4$, or pharmaceutically acceptable carrier anion such as citrate, tartrate
X=Au$_n$—[S—CH$_2$(CH$_2$)$_9$CH$_2$—(OCH$_2$CH$_2$)$_4$O]
COCH$_2$CH$_2$-phenyl-O, or
Au$_n$—[S—(CH$_2$)$_9$—S n=a subscript meaning n=1-20 atoms

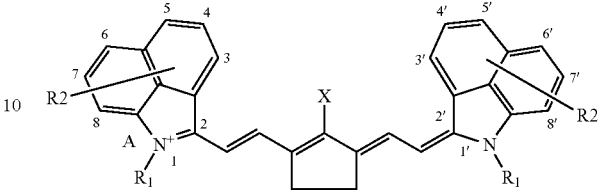

Formula 8

R2=H, EWG, EDG in 3, 3', 4, 4', 5, 5', 6, 6', 7, 7', 8, 8' positions
R1=H, Alkyl, Aryl, Aralkyl, RSO$_3^-$, RCOO$^-$, RNH$_2$
A=I, Cl, Br, OSO$_2$Aryl, OSO$_2$R, BF$_4$, ClO$_4$, or pharmaceutically acceptable carrier anion such as citrate, tartrate
X=Au$_n$—[S—CH$_2$(CH$_2$)$_9$CH$_2$—(OCH$_2$CH$_2$)$_4$O]
COCH$_2$CH$_2$-phenyl-O, or
Au$_n$—[S—(CH$_2$)$_9$—S n=a subscript meaning n=1-20 atoms

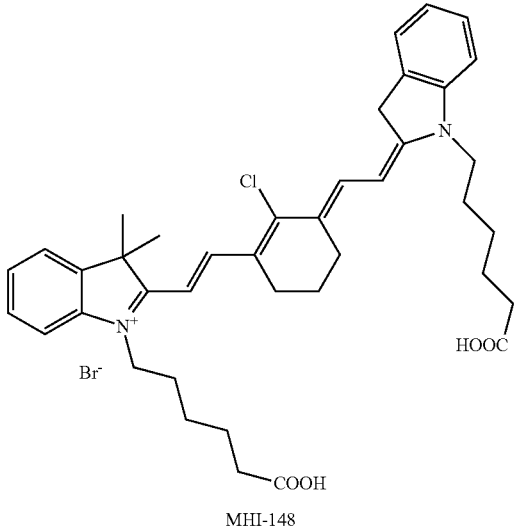 [SMILES: CC1(C)C(/C=C/C2=C(Cl)C(=C/C=C3\Cc4ccccc4N3CCCCCC(=O)O)/CCC2)=[N+](CCCCCC(=O)O)c2ccccc21 ; [Br-]]

MHI-148

Formula 1 shows cyanine dyes having the most basic structure of MHI-148 with a Au$_n$—[S—CH$_2$(CH$_2$)$_9$CH$_2$—(OCH$_2$CH$_2$)$_4$O]COCH$_2$CH$_2$-phenyl-O group on a cyclohexene ring that imparts activity to the cancer cell binding and destruction processes. In this embodiment, when X is Au$_n$—[S—CH$_2$(CH$_2$)$_9$CH$_2$—(OCH$_2$CH$_2$)$_4$O] COCH$_2$CH$_2$-phenyl-O group, the maximum absorbance wavelength is between 770 and 780 nm, depending on the solvent and the maximum emission wavelength (maximum quantum yield and lambda fluorescent light) is between 805 and 820 depending on the solvent.

Formula 2 shows cyanine dyes having an extended conjugation in the heterocyclic moiety and containing cyclopentene ring. In this embodiment, when X is a Au$_n$—[S—CH$_2$(CH$_2$)$_9$CH$_2$—(OCH$_2$CH$_2$)$_4$O]COCH$_2$CH$_2$-phenyl-O group, the maximum absorbance wavelength is between 790 and 800 nm, depending on the solvent and the maximum emission wavelength (maximum quantum yield and lambda fluorescent light) is between 810 and 820 nm depending on the solvent. This extended conjugation slightly increases the absorption and emission wavelengths and at the same time increases the hydrophobicity of the molecule that seems to be an important factor in dye retention by the cancer cells.

Formula 3 shows cyanine dyes having a five member ring in the center of the molecule. In this embodiment, when X is with a $Au_n$—[S—$CH_2(CH_2)_9CH_2$—$(OCH_2CH_2)_4O$]$COCH_2CH_2$-phenyl-O group, the maximum absorbance wavelength is between 770 and 790 nm, depending on the solvent and the maximum emission wavelength (maximum quantum yield and lambda fluorescent light) is between 790 and 810 nm, depending on the solvent. The five member ring may slightly increase the reactivity of the halogen for reactions leading to Au dyes. Note, the kill mechanism in this invention is RF energy and localized heating of cancer cells near to the Au dye.

Formula 4 shows cyanine dyes having an extended conjugation in the heterocyclic moiety and containing the five member central ring. In this embodiment, when X is $Au_n$—[S—$CH_2(CH_2)_9CH_2$—$(OCH_2CH_2)_4O$]$COCH_2CH_2$-phenyl-O group, the maximum absorbance wavelength is between 770 and 790 nm, depending on the solvent and the maximum emission wavelength (maximum quantum yield and lambda fluorescent light) is between 790 and 810 nm depending on the solvent. This extended conjugation slightly increases the absorption and emission wavelengths and at the same time increases the hydrophobicity of the molecule that seems to be an important factor in dye retention by the cancer cells.

Formula 5 shows cyanine dyes having an extended conjugation in the heterocyclic moiety and containing the six member central ring. In this embodiment, when X is $Au_n$—[S—$CH_2(CH_2)_9CH_2$—$(OCH_2CH_2)_4O$]$COCH_2CH_2$-phenyl-O group, the maximum absorbance wavelength is between 770 and 790 nm, depending on the solvent and the maximum emission wavelength (maximum quantum yield and lambda fluorescent light) is between 790 and 810 nm depending on the solvent. This extended conjugation slightly increases the absorption and emission wavelengths and at the same time increases the hydrophobicity of the molecule that seems to be an important factor in dye retention by the cancer cells.

Formula 6 shows cyanine dyes having an extended conjugation in the heterocyclic moiety and containing the five member central ring. In this embodiment, when X is $Au_n$—[S—$CH_2(CH_2)_9CH_2$—$(OCH_2CH_2)_4O$]$COCH_2CH_2$-phenyl-O group, the maximum absorbance wavelength is between 770 and 810 nm, depending on the solvent and the maximum emission wavelength (maximum quantum yield and lambda fluorescent light) is between 790 and 810 nm depending on the solvent. This extended conjugation slightly increases the absorption and emission wavelengths and at the same time increases the hydrophobicity of the molecule that seems to be an important factor in dye retention by the cancer cells.

Formula 7 shows synthesized cyanine dyes having an extended conjugation in the heterocyclic moiety and containing the six member central ring. In this embodiment, when X is $Au_n$—[S—$CH_2(CH_2)_9CH_2$—$(OCH_2CH_2)_4O$]$COCH_2CH_2$-phenyl-O group, the maximum absorbance wavelength is between 980 and 1000 nm, depending on the solvent and the maximum emission wavelength (maximum quantum yield and lambda fluorescent light) is between 1000 and 1020 nm depending on the solvent. This extended conjugation substantially increases the absorption and emission wavelengths and at the same time increases the hydrophobicity of the molecule that seems to be an important factor in dye retention by the cancer cells.

Formula 8 shows synthesized cyanine dyes having an extended conjugation in the heterocyclic moiety and containing the five member central ring. In this embodiment, when X is $Au_n$—[S—$CH_2(CH_2)_9CH_2$—$(OCH_2CH_2)_4O$]$COCH_2CH_2$-phenyl-O group, the maximum absorbance wavelength is between 980 and 1000 nm, depending on the solvent and the maximum emission wavelength (maximum quantum yield and lambda fluorescent light) is between 1000 and 1020 nm depending on the solvent. This extended conjugation substantially increases the absorption and emission wavelengths and at the same time increases the hydrophobicity of the molecule that seems to be an important factor in dye retention by the cancer cells.

Other suitable dyes include but not limited to unsymmetrical tricarbocyanine, pentacyanine and heptacyanine structures functionalized with gold nanoparticles 3.5-5 nm (TEM) as indicated in Formula 9 which absorb light having the wavelengths in the region of 680 to 760 nm.

Formula 9

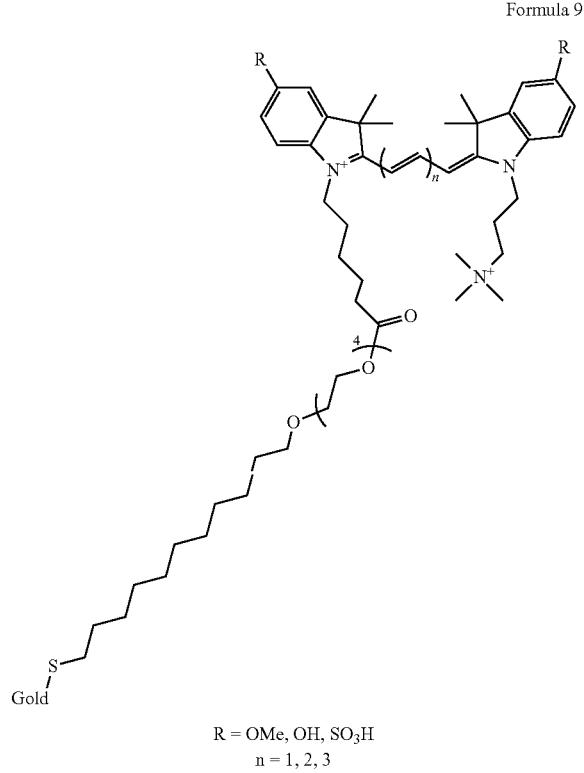

R = OMe, OH, SO$_3$H
n = 1, 2, 3

Formulas 1-9 show a variety of carbocyanines dyes attached to a metal nanoparticle (gold dye) that selectively attach to cancer cell. The carbocyanine dye fluoresces in the near infrared range and can be activated by light in the near infrared spectrum. These gold dyes are quickly flushed from the body except for those molecules that attach to cancer cells. When the gold dye is attached to a cancer cell or cancerous tissue and a RF field is applied the cancers material undergoes hyperthermia and is destroyed. Very little of the surrounding healthy tissue is affected.

Thus there has been described an improved method of treating cancer that does not have the side effects of chemotherapy or radiation treatment and in which the energy used to kill the cancer cells can be highly targeted.

While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

What is claimed is:

1. A method of detecting and destroying cancer cells, comprising:
    introducing a composition into an organism suspected of having cancer cells;
        wherein said composition comprises a carbocyanine dye covalently attached to a metal nanoparticle via a linker bound to a cyclohexene ring or a cyclopentene ring of said carbocyanine dye;
        wherein said linker comprises a polyethylene group; and
        wherein said composition selectively binds to said cancer cells;
    shining a near infrared light on a region suspected of having said cancer cells;
    detecting a fluorescence from said composition to locate said cancer cells; and
    targeting a beam of radio frequency energy at said region to induce hyperthermia in said cancer cells.

2. The method of claim 1, wherein said fluorescence is emitted by said carbocyanine dye.

3. The method of claim 1, wherein said composition does not bind to healthy cells.

4. The method of claim 1, wherein said carbocyanine dye absorbs light having a wavelength ranging from between about 680 nanometers to about 1200 nanometers.

5. The method of claim 1, wherein said carbocyanine dye comprises a heptamethine cyanine dye.

6. The method of claim 5, wherein said heptamethine cyanine dye absorbs light having a wavelength ranging from between about 780 nanometers to about 1100 nanometers.

7. The method of claim 1, wherein said induction of hyperthermia is facilitated by said metal nanoparticle.

8. The method of claim 1, wherein said metal nanoparticle comprises a gold nanoparticle.

9. The method of claim 1, wherein said metal nanoparticle has a diameter of less than about 100 micrometers.

10. The method of claim 1, wherein said linker comprises a sulfur.

11. The method of claim 1, wherein said carbocyanine dye has a structure selected from the group consisting of: tricarbocyanine, pentacarbocyanine and heptacarbocyanine.

12. A method of detecting and destroying cancer cells, comprising:
    introducing a composition into an organism suspected of having cancer cells;
        wherein said composition comprises a carbocyanine dye covalently attached to a metal nanoparticle via a linker bound to a nitrogen of an indole moiety of said carbocyanine dye;
        wherein said linker comprises a polyethylene group; and
        wherein said composition selectively binds to said cancer cells;
    shining a near infrared light on a region suspected of having said cancer cells;
    detecting a fluorescence from said composition to locate said cancer cells; and
    targeting a beam of radio frequency energy at said region to induce hyperthermia in said cancer cells.

13. The method of claim 12, wherein said fluorescence is emitted by said carbocyanine dye.

14. The method of claim 12, wherein said composition does not bind to healthy cells.

15. The method of claim 12, wherein said carbocyanine dye absorbs light having a wavelength ranging from between about 680 nanometers to about 1200 nanometers.

16. The method of claim 12, wherein said carbocyanine dye comprises a heptamethine cyanine dye.

17. The method of claim 16, wherein said heptamethine cyanine dye absorbs light having a wavelength ranging from between about 780 nanometers to about 1100 nanometers.

18. The method of claim 12, wherein said induction of hyperthermia is facilitated by said metal nanoparticle.

19. The method of claim 12, wherein said metal nanoparticle comprises a gold nanoparticle.

20. The method of claim 12, wherein said metal nanoparticle has a diameter of less than about 100 micrometers.

21. The method of claim 12, wherein said linker comprises a sulfur.

22. The method of claim 12, wherein said carbocyanine dye has a structure selected from the group consisting of: tricarbocyanine, pentacarbocyanine and heptacarbocyanine.

* * * * *